United States Patent [19]
Fletcher et al.

[11] Patent Number: 6,019,602
[45] Date of Patent: Feb. 1, 2000

[54] TOOTH ROOT TIP EXTRACTOR

[76] Inventors: Tarrie Fletcher, Rte. 3, Box 2702, Lakeside, Ariz. 85929; Jeffery D. Orr, 611 Solitude Cir., Payson, Ariz. 85541

[21] Appl. No.: 09/167,096

[22] Filed: Oct. 5, 1998

[51] Int. Cl.$^7$ .................................................... A61C 3/00
[52] U.S. Cl. ........................... 433/152; 433/130; 433/165
[58] Field of Search ................................... 433/102, 130, 433/224, 128, 165, 141, 144, 146, 147, 152

[56] References Cited

U.S. PATENT DOCUMENTS

| 5,865 | 10/1848 | Dubs | 433/152 |
|---|---|---|---|
| 462,896 | 11/1891 | Eddy | 433/128 |
| 723,710 | 3/1903 | McCune | 433/147 |
| 772,324 | 10/1904 | Asdell | 433/152 |
| 1,771,182 | 7/1930 | Lentulo | 433/224 |
| 2,210,349 | 8/1940 | Van Beeck | 433/152 |
| 3,555,685 | 1/1971 | Loge | 433/102 |
| 3,578,745 | 5/1971 | Garnier | 433/102 |
| 4,021,920 | 5/1977 | Kirschner et al. | 433/165 |
| 4,230,454 | 10/1980 | Lococo | 433/153 |
| 4,443,196 | 4/1984 | Rico | 433/158 |
| 4,627,817 | 12/1986 | Higa | 433/152 |
| 5,575,650 | 11/1996 | Niznick et al. | 433/165 |
| 5,735,689 | 4/1998 | McSpadden | 433/102 |

*Primary Examiner*—Jeffrey A. Smith
*Attorney, Agent, or Firm*—Clayton, Howarth & Cannon P.C.

[57] ABSTRACT

An extraction device for extracting some or all of a tooth from a patient, such as the root of the tooth. One embodiment of the device includes an extraction bit having helical windings without a linear core portion separate from the windings, and in that manner is distinguishable from a common screw. The extraction bit may include a partial-spiral flute or groove formed in a tip thereof. A lockable and releaseable hand piece for attaching to the extraction bit provides leverage to the user for dislodging the tooth root, and is reversible in its attachment position to the extraction bit.

48 Claims, 3 Drawing Sheets

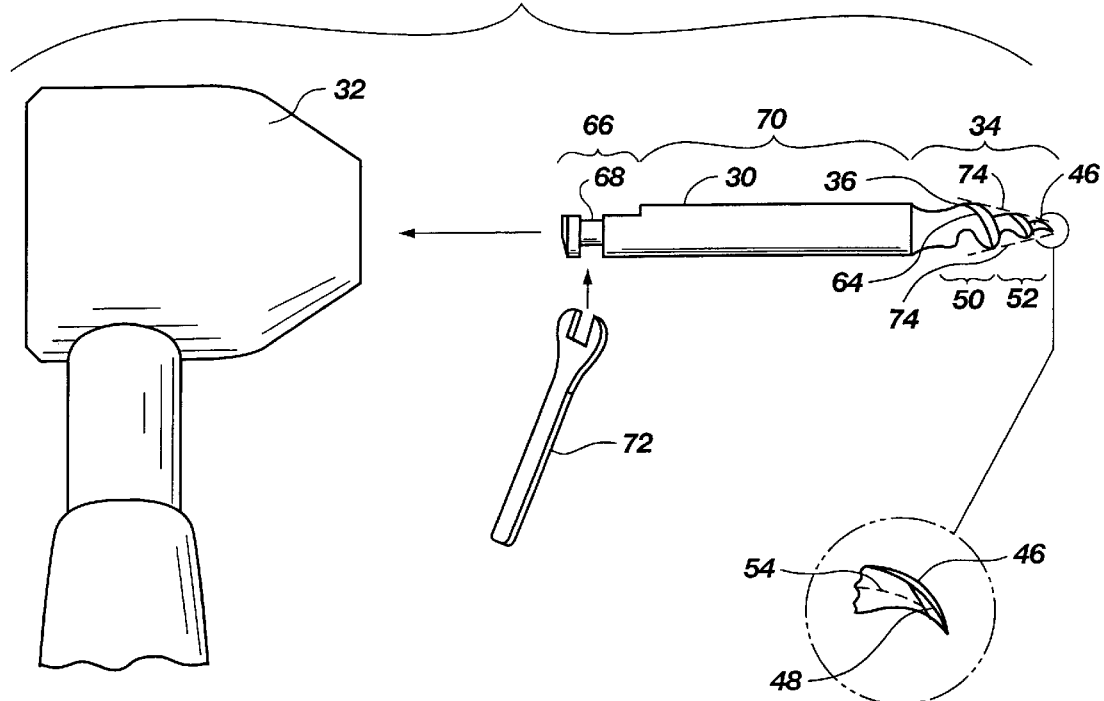
Fig. 5
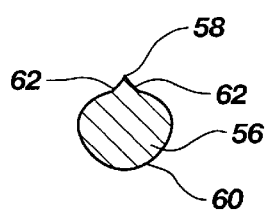
Fig. 6
Fig. 7
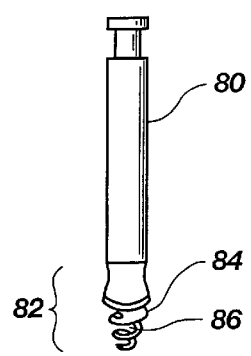
Fig. 8
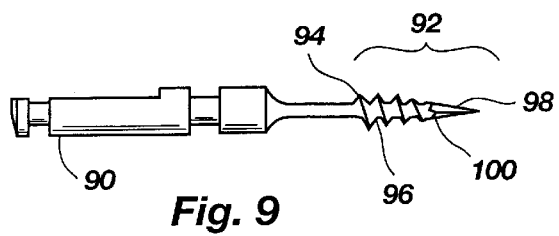
Fig. 9

TOOTH ROOT TIP EXTRACTOR

BACKGROUND OF THE INVENTION

1. The Field of the Invention

The present invention relates generally to tooth extraction devices. More particularly, it concerns a tooth root tip extractor for extracting severed tooth roots from the mouth of a patient.

2. The Background Art

A problem occurs in the field of dentistry when the crown of a tooth breaks apart from the root of the tooth, leaving the root behind and embedded in the bone. This can occur in several different settings, such as during a formal tooth extraction procedure by a dentist, or when the crown of a tooth is inadvertently fractured loose during heaving physical activity, or in any other manner.

FIG. 1 illustrates schematically a jaw bone 14, gum tissue 16, tooth crown 18 and a nerve 20 of the tooth 10. The root 12 of the tooth 10 often fuses directly to the jaw bone 14, which causes the root 12 to break along severance path 22 during extraction or fracturing of the tooth 10. FIG. 2 shows the condition of a tooth root 12 that has been left behind after removal of the majority of the tooth 10 of FIG. 1. A substantial amount of effort is required to extract the severed tip of the root 12, especially when it has fused with the jaw bone 14.

Conventional methods of extracting the broken tip of the root 12 include simply drilling out part of the jaw bone 14, then digging out the root tip with a sharp member known as a tooth root "pick" or "elevator." Such prior art tooth root extraction procedures are astonishingly unsophisticated, and perhaps even barbaric in nature, and yet they are still being used today. As shown in FIG. 2, pick 24 is applied to simply pry the severed tooth root 12 loose from the jaw bone 14, which often causes painful damage to surrounding gum tissue 16 and to the jaw bone 14.

In some cases, dentists will loosen the tooth root 12 with the pick 24, then use a root pick elevator to elevate the tooth root 12 and a forceps 26 (FIG. 3) to grasp the tooth root 12 and extract it. This requires the dentist to drill out a sufficient amount of jaw bone 14 with a conventional dental drill to make room for the bulky forceps 26 and root pick elevator to access the tooth root 12.

Such procedures cause a lot of the jaw bone 14 and associated nerves and blood vessels to be needlessly removed and damaged sometimes causing a "dry socket" condition which prevents blood from clotting in the extraction site. There is of course increased trauma to the patient, and a slower healing process, as a result. These prior art procedures are not only barbaric but also require a lot of time, and therefore more money in terms of the dentist's time to perform the procedure.

Attempts have been made to overcome the disadvantages of using the tooth root pick 24 and forceps 26. For example, U.S. Pat. Nos. 2,210,349 (issued on Aug. 6, 1940 to Van Beeck) and 4,443,196 (issued Apr. 17, 1984 to Rico) illustrate tooth root extractors having a threaded screw-like member that can be rotatably screwed into the tooth root and lodged therein, after which the user extracts the screw-like member and thereby lifts the root from the jaw bone.

Such devices have not caught on in the field of dentistry, and are characterized by disadvantages. The screw member introduces a splitting action within the tooth root as it is wedged into the tooth root, and thereby achieves an unstable grip within the tooth in some cases. Sometimes the screwing and splitting action will actually cause the root to split apart prematurely, thereby further complicating the extraction procedure.

OBJECTS AND SUMMARY OF THE INVENTION

It is therefore an object of the present invention to provide an extraction device capable of extracting tooth roots without removing portions of the jaw bone or associated nerves or blood vessels or tissue.

It is a further object of the present invention to provide such an extraction device that is simple in design and manufacture.

It is another object of the present invention to provide such an extraction device which results in less patient healing time.

It is a further object of the present invention, in accordance with one aspect thereof, to provide an extraction device which reduces splitting action in a tooth root being extracted therewith.

The above objects and others not specifically recited are realized in a specific illustrative embodiment of an extraction device for extracting some or all of a tooth from a patient, such as the root of the tooth. One embodiment of the device includes an extraction bit having helical windings without a linear core portion separate from the windings, and in that manner is distinguishable from a common screw. The extraction bit may include a partial-spiral flute or groove formed in a tip thereof. A lockable and releaseable hand piece for attaching to the extraction bit provides leverage to the user for dislodging the tooth root, and is reversible in its attachment position to the extraction bit.

Additional objects and advantages of the invention will be set forth in the description which follows, and in part will be apparent from the description, or may be learned by the practice of the invention without undue experimentation. The objects and advantages of the invention may be realized and obtained by means of the instruments and combinations particularly pointed out in the appended claims.

BRIEF DESCRIPTION OF THE DRAWINGS

The above and other objects, features and advantages of the invention will become apparent from a consideration of the subsequent detailed description presented in connection with the accompanying drawings in which:

FIG. 5 is a side view of an extraction bit made in accordance with the principles of the present invention, as part of an exploded view of the bit in conjunction with a conventional dental drill and gripping tool;

FIG. 6 is an enlarged view of a distal tip portion of the extraction bit of FIG. 5;

FIG. 7 is a cross-sectional view of a helical section of the extraction bit of FIG. 5;

FIG. 8 is a side view of an alternative embodiment of the extraction bit of FIG. 5;

FIG. 9 is a side view of another alternative embodiment of the extraction bit of FIG. 5;

DETAILED DESCRIPTION

Figure 1:
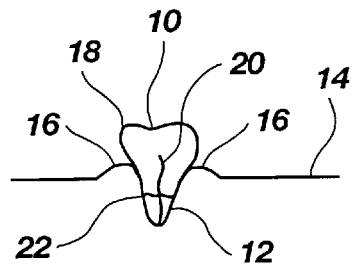
FIG. 1 is a schematic view of a tooth residing in the jaw bone of a patient.

For the purposes of promoting an understanding of the principles in accordance with the invention, reference will now be made to the embodiments illustrated in the drawings and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would normally occur to one skilled in the relevant art and having possession of this disclosure, are to be considered within the scope of the invention claimed.

Applicant has discovered that the process of extracting a severed tooth root from the mouth of a patient is enhanced significantly by using a special helical extraction bit with a fluted tip. The special extraction bit is applied to the severed tooth root with a conventional dental drill. As the bit penetrates the tooth root, it burrows into the root and its special design causes it to dislodge and displace tooth root particulates from the root as it burrows, thereby reducing and even eliminating splitting action within the tooth root, and without removing any part of the jaw bone.

The disadvantages described above in conjunction with the prior art tooth root extraction devices are overcome by the invention shown in FIGS. 4–11. Before discussing the operation and further advantages of the invention, it is thought proper to explain the structural aspects of the invention, as illustrated in the accompanying drawings, in detail.

Figure 4:
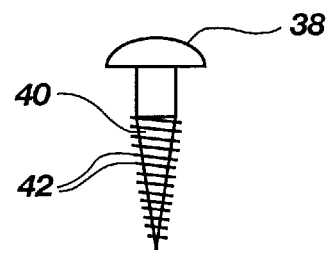
FIG. 4 is a side view of a conventional wood screw as known in the prior art.
Figure 3:
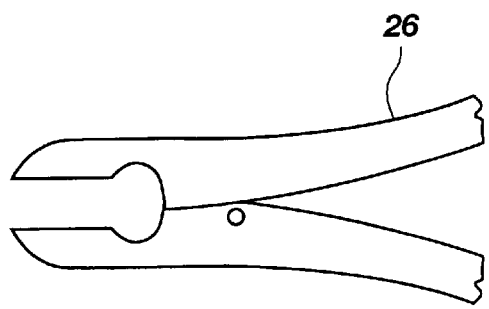
FIG. 3 is a schematic view of a prior art tooth root extraction forceps.

Referring to FIG. 5, an extraction bit 30 is inserted into a conventional dental drill 32. The bit 30 terminates in a distal body 34 comprising a plurality of substantially helical windings 36 extending in a generally proximal-to-distal direction helical winding. At least a majority length of the distal body 34 is characterized by an absence of an elongate linear core portion such as a solid or hollow cylindrical core, for example separate from the helical windings 36. Although the distal body 34 does not actually have a hollow core portion, the helical windings 36 characterize the entire distal body 34, as opposed to a conventional wood screw 38 as shown in FIG. 4 which has a linear core portion 40 separate from and in addition to its conventional threads 42.

Although the windings 36 are presently preferred, the principles of the present invention also include the alternative windings shown in FIG. 8. More specifically, FIG. 8 shows an extraction bit 80 having a distal body 82 comprised of helical windings 84 that surround a central core space 86, as opposed to the windings 36 of FIG. 5 which do not define a central core space. Of course, neither the distal body 34 of FIG. 5 nor the distal body 82 of FIG. 8 include an elongate linear core portion separate from the helical windings 36 (FIG. 5) or 84 (FIG. 8), respectively. This structural aspect of having helical windings without having a separate elongate linear core portion distinguishes the embodiments of FIGS. 5 and 8 from common screw 38 shown in FIG. 4, said screw 38 having the separate linear core portion 40 in addition to windings or threads 42 that are formed upon the core portion 40. The windings 36 of FIG. 5 are not formed upon a core portion since there is no separate core portion, even though the windings 36 may not define a hollow core space like the core space 86 defined by the windings 84 in FIG. 8.

Stated another way, the helical windings 36 of FIG. 5 define a substantially helical axis (shown most clearly as item 54 in FIG. 6) without the windings 36 surrounding a central core space, as opposed to the windings 84 of FIG. 8 which do indeed surround the central core space 86. The helical windings 36 of FIG. 5 and the helical windings 84 of FIG. 8 preferably comprise less than five windings. It is further preferable that the windings 36 and 84 define a linear length, such as indicated by brackets 34 and 82, respectively, that is greater than one-tenth and less than one-half of a length of the extraction bits 30 and 80, respectively.

Referring now to FIG. 9, it is further shown that the principles of the present invention also include an extraction bit 90 having a distal body 92 which includes helical windings 94 formed upon and surrounding a separate linear core portion 96, as opposed to the windings 36 and 84 of FIGS. 5 and 8, respectively, which do not have any such linear core portion.

The helical windings 94 preferably terminate in a tip portion 98 which has an open recess 100 formed therein. The open recess 100 is preferably a partial-spiral groove. The recess 100 is formed in the sides of the windings 94 and in a distal half of the distal body 92. The recess 100 is preferably in a section of winding that comprises less than one-half of one winding, preferably less than one-third of one winding, more preferably less than one-fourth of one winding, and most preferably less than one-fifth of one winding. The recess 100 comprises an elongate shape that extends in a generally nonparallel direction with respect to a helical axis of the windings 94.

The conventional dental drill 32 of FIG. 5 is operable to rotate the bit 30 as known to those of ordinary skill in the field of dentistry. The drill 32 may therefore be described as a rotating means for rotating the bit 30 to thereby embed at least a portion of the distal body 34 into the root 12 (FIGS. 1–2) of a tooth. The dental drill 32 is also described as a motorized boring instrument.

Referring now more particularly to FIGS. 5 and 6, the helical windings 36 preferably terminate in a tip portion 46 which has an open recess 48 formed therein. The open recess 48 is preferably a partial-spiral groove. The helical windings 36 comprise a proximal half 50 and a distal half 52, and the recess 48 is formed in the sides of the windings 36 and in the distal half 52 of said distal body 34. The recess 48 is preferably formed in a distal-most portion of the windings 36, in a section of winding that comprises less than one-half of one winding, preferably less than one-third of one winding, more preferably less than one-fourth of one winding, and most preferably less than one-fifth of one winding.

The helical windings 36 define a substantially helical axis 54. The recess 48 comprises an elongate shape that extends in a generally nonparallel direction with respect to the helical axis 54, as shown in FIG. 6.

Referring now to FIGS. 5–7, a cross-section of the helical windings 36 taken orthogonal to the helical axis 54 comprises a teardrop shape 56 as shown in FIG. 7. The teardrop shape 56 has a single point 58 at one end thereof. Preferably, an exterior perimeter 60 of the cross-sectional teardrop shape 56 includes two opposing concave sections 62 that are adjoined to form the single point 58. The teardrop shape 56 is preferably substantially symmetrical.

The single point 58 of the cross-sectional teardrop shape 56 indicates a helical exterior edge 64 that is formed on the distal body 34. The helical edge 64 is preferably sharpened to accomplish a cutting action therewith when the distal body 34 is rotatably embedded into the tooth root 12.

The bit 30 further includes a proximal portion 66 having an at least partially annular recess 68 formed therein, and a central portion 70 interconnecting the proximal portion 66 and the distal body 34. The central portion 70 and proximal portion 66 are preferably characterized by an absence of threads formed thereon.

As shown most clearly in FIG. 5, the helical windings 36 define a surrounding outer boundary, represented schematically by dashed lines 74, that tapers radially inwardly in a proximal-to-distal direction. The windings 36 may alternatively define a surrounding outer boundary having a substantially constant radius along a majority length of said windings.

Figure 2:
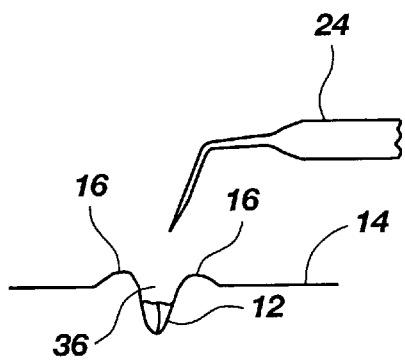
FIG. 2 is a schematic view of a prior art tooth root pick or elevator.
Figure 10:
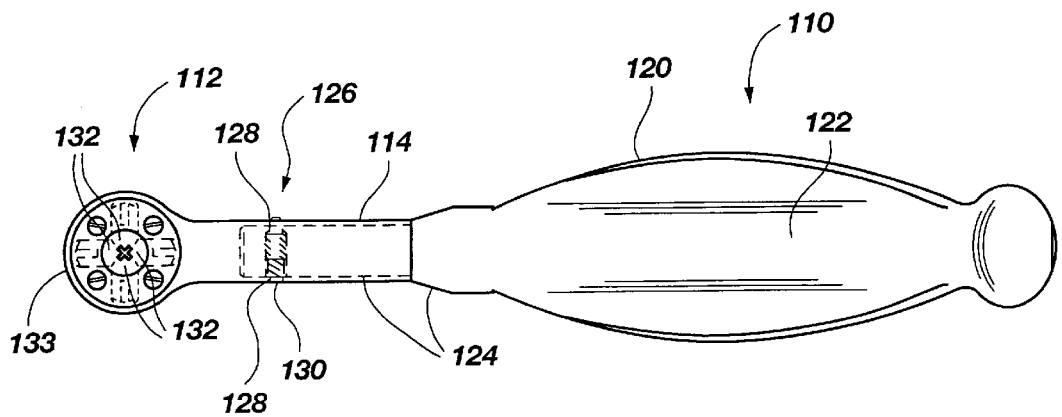
FIG. 10 is a plan view of a hand piece for attaching to the extraction bit of FIG. 5, made in accordance with the principles of the present invention.
Figure 11:
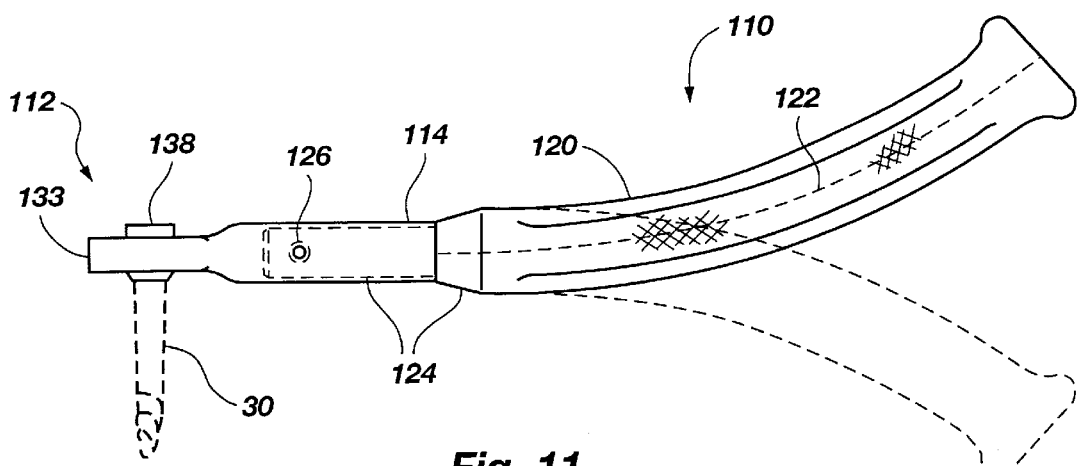
FIG. 11 is a side view of the hand piece of FIG. 10.
Figure 12:
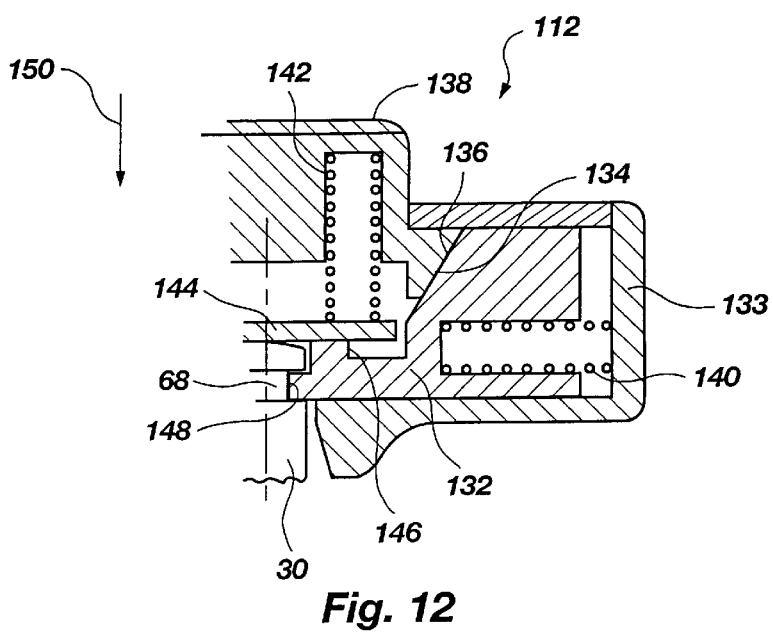
FIG. 12 is a partial, cross-sectional view of a head portion of the hand piece of FIGS. 10.

Referring now to FIGS. 10–12, the invention further includes a hand piece 110, which operates as an extraction means for extracting the extraction bit 30 of FIG. 5 and the tooth root 12 of FIG. 2 from a mouth of a patient. The hand piece 110 includes a head 112, which operates as a gripping means for gripping the extraction bit 30 when said bit 30 is embedded in the tooth root 12, such that a proximal portion 114 of said gripping means (head 112) extends laterally outward from the bit 30 (shown in phantom line in FIG. 11).

The hand piece 110 further includes a handle means 120 defining a central axis 122 at a distal end 124 thereof for receiving the proximal portion 114 of the head 112 on said distal end 124. A locking means 126, preferably disposed on the distal end 124 of the handle means 120, is provided for locking said proximal portion 114 of the head 112 to said handle means 120 at any of a plurality of selectable positions of said proximal portion 114 about the central axis 122 of the handle means 120. Accordingly, the handle means 120 and the head 112 are releasably attached to one another, preferably by the locking means 126.

The handle means 120 preferably comprises an elongate, reversible handle member defining an arch, as shown most clearly in FIG. 11. The locking means 126 preferably comprises a spring-loaded pin member disposed in the distal end 124 of the handle means 120. The proximal portion 114 of the head 112 includes one or more apertures 128 formed therein, configured and positioned to be aligned with the spring-loaded pin 126.

Accordingly, the user may adjust the position of the head 112 about the axis 122 of the handle means 120 by simply depressing the spring-loaded pin 126 and rotating the head 112 relative to the distal end 124 of the handle means 120 about the axis 112, until the spring-loaded pin 126 is aligned with a desired aperture 128 at which time the pin 126 is ejected through said aperture 128 by the spring portion 130 to thereby releasably secure the head 112 in position relative to the handle means 120.

The proximal end 114 of the head 112 includes a receiving chamber formed therein, said receiving chamber being configured and adapted to receive the distal end 124 of the handle means 120. The apertures 128 are formed in sidewalls of the proximal end 114 for receiving the pin member 126 therethrough when aligned with said pin member 126. The invention may be designed to have two apertures 128 positioned opposite one another on opposing sides of the proximal end 114, to thereby permit 180-degree reversibility of the head 112 relative to the handle means 120. Alternatively, there may be several apertures 128 formed in the proximal end 114 of the head 112.

The head 112 preferably includes a plurality of sliding members 132 and a means for (i) sliding said sliding members 132 radially inwardly into a locking position about the bit 130 and (ii) sliding said sliding members 132 radially outwardly into a releasing position.

The operative features of the head 112 are shown more clearly in FIG. 12. The sliding members 132 each include a beveled contacting face 134 which engages a corresponding beveled contacting face 136 of a button 138. As shown in FIG. 10, there are preferably four separate sliding members 132 slidably disposed in the casing 133 of the head 112, each sliding member being biased by a lateral spring member 140 shown in FIG. 12. The button 138 thus rests upon the beveled contacting faces 134 of the sliding members 132, and also upon axial spring members 142. The axial spring members 142 are disposed between the button 138 and a stopping plate 144, said stopping plate 144 in turn resting in slidable engagement upon ribs 146 of the sliding members 132.

As such, when the extraction bit 30 is inserted into the head 112, it abuts the stopping plate 144 which holds the bit 30 into a position with the annular recess 68 being in alignment with lateral contacting faces 148 of the sliding members 132. The button 138 must be pressed downwardly (in the direction indicated by arrow 150) to force the sliding members radially outwardly by engagement along the beveled contacting planes between surfaces 134 and 136, to thereby remove the lateral contacting faces 148 sufficiently to permit insertion of the bit 30 into the head 112 and against the stopping plate 144. Once the bit 30 resides against the plate 144 with the annular recess 68 in alignment with the lateral contacting faces 148 of the sliding members 132, and button 138 is released by the user to permit the lateral contacting faces 148 of the sliding members 132 to slide into position within the annular recess 68 of the bit 30, thereby releasably locking the bit 30 within the head 112.

In operation, the bit 30 is inserted within the dental drill 32, which the operator actuates to induce either a low-speed or high-speed rotational movement to the bit 30 about its elongate axis. The operator, typically a dentist, then applies the rotating bit 30 to the severed root 12 shown in FIG. 2.

Once a sufficient portion of the windings 36 of the bit 30 has been properly embedded into the tooth root 12 with the drill 32, the drill 32 is removed. The bit 30 may be further turned by hand, or with the aid of a manually operable gripping tool 72 which might illustratively comprise a wrench, in order to refine the position of the bit 30 within the tooth root 12. The gripping tool 72 is thus configured and adapted for gripping the bit 30 when the bit 30 is at least partially embedded within a portion of the tooth of a patient, such as the root 12.

When the bit 30 is properly lodged within the severed root 12 to the operator's satisfaction, the hand piece 110 is locked in place to the proximal end 66 of the bit 30. At this point the handle means 120 is extending laterally outwardly from the bit 30. The operator simply grasps the handle means 120 to lift and elevate the tooth root 12 from the mouth of the patient. The head 112 of the hand piece 110 and its internal working structure as explained above collectively provide the advantages of a quick engagement and release of the head 112 to the bit 30. The operator simply presses the button 130 to slide the sliding members 132 radially outwardly enough to permit entry of the proximal end 66 of the bit 30 into the head and into position against the stopping plate 144 as shown in FIG. 12.

The arch of the handle means 120 aids the operator in providing an optimal lifting force to the tooth root 12, in that the operator may choose whichever point along the arched portion is optimal according to experience to grip and lift as may best suit the particular position of the root 12 and the configuration of the patient's mouth (not shown).

The operator will likely prefer to position the arch of the handle means 120 to extend upwardly from the patient's mouth when extracting a root from the upper teeth of the patient. The handle means 120 is conversely positioned downwardly from the patient's mouth when extracting a root from the lower teeth. The versatility of applicant's invention permits the operator to use the single hand piece 110 regardless of whether the severed root to be extracted resides among the upper or lower teeth. The handle means 120 may also be re-positioned with respect to the head 112, by utilizing the locking means 126 as explained above.

Accordingly, the extraction bit 30 may be described as an embedding means for becoming at least partially embedded within a portion of the tooth root 12 of a patient, said embedding means terminating in a distal body 34 comprising a plurality of substantially helical windings 36 extending in a generally proximal-to-distal direction, wherein at least a majority length of said distal body 34 is characterized by an absence of an elongate linear core portion separate from said helical windings 36.

It will be appreciated that the structure and apparatus disclosed herein in the form of the bits 30, 80 and 90 are merely examples of embedding means within the principles of the present invention, and it should be appreciated that any structure, apparatus or system for embedding which operates the same as, or equivalent to, those disclosed herein are intended to fall within the scope of an embedding means as applied to tooth extraction, including those structures, apparatus or systems for embedding which are presently known, or which may become available in the future. Anything which functions the same as, or equivalently to, an embedding means as described herein falls within the scope of this element.

In accordance with the features and combinations described above, a preferred method of extracting at least a portion of a tooth from a mouth of a patient comprises the steps of:

(a) boring a hole into the portion of the tooth with a boring instrument and displacing tooth particulates with said boring instrument, as said hole is being bored, without splitting said portion of the tooth, and lodging the boring instrument into a position of stability in the portion of the tooth; and (b) extracting the portion of the tooth by retracting the boring instrument from the mouth of the patient.

Another method of extracting at least a portion of a tooth from a mouth of a patient comprises the steps of:

(a) boring a hole into the portion of the tooth with a motorized boring instrument having a partial-spiral flute formed in a tip section thereof without removing any portion of a jaw bone of the patient, and lodging at least a portion of the boring instrument into a position of stability in the portion of the tooth; and (b) extracting the portion of the tooth by retracting the boring instrument from the mouth of the patient.

A still further method of extracting[]at least a portion of a tooth from a mouth of a patient comprises the steps of:

(a) inserting a bit into a motorized boring instrument;

(b) activating the motorized boring instrument and boring the bit into the portion of the tooth and lodging at least a portion of the bit into a position of stability in the portion of the tooth;

(c) attaching an arched handle to the bit; and (d) extracting the portion of the tooth by elevating the arched handle without maintaining any force-distributing member in a static position against any teeth of the patient.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been shown in the drawings and fully described above with particularity and detail in connection with what is presently deemed to be the most practical and preferred embodiment(s) of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. An extraction device for extracting at least a portion of a tooth from a patient, said extraction device comprising:

embedding means for becoming at least partially embedded within a portion of a tooth of a patient, said embedding means terminating in a distal body consisting of a plurality of substantially helical windings extending in a generally proximal-to-distal direction, such that said distal body is formed entirely of helical windings, said windings being sufficiently rigid to enable the distal body to become forcibly embedded in the portion of a tooth, and wherein the distal body is further characterized by an absence of a cylindrical, elongate linear core portion; and rotating means for rotating the embedding means to thereby embed at least a portion of the distal body of said embedding means into the portion of the tooth.

2. The extraction device of claim 1, wherein the helical windings terminate in a tip portion having an open recess formed therein.

3. The extraction device of claim 2, wherein the recess comprises a partial-spiral groove.

4. The extraction device of claim 2, wherein the helical windings define a substantially helical axis, and wherein the recess comprises an elongate shape that extends in a generally nonparallel direction with respect to the helical axis.

5. The extraction device of claim 1, wherein the embedding means comprises a bit that includes the distal body, said bit further including a proximal portion having an at least partially annular recess formed therein, and a central portion interconnecting the proximal portion and the distal body, said central portion and proximal portion being characterized by an absence of threads formed thereon.

6. The extraction device of claim 1, wherein the rotating means comprises a motorized boring instrument.

7. The extraction device of claim 1, wherein the embedding means further comprises a helical exterior edge formed on the distal body.

8. The extraction device of claim 7, wherein the helical exterior edge is sharpened.

9. The extraction device of claim 1, wherein the helical windings define a surrounding outer boundary having a substantially constant radius along a majority length of said windings.

10. The extraction device of claim 1, wherein the distal body further comprises helical windings surrounding a central core space.

11. The extraction device of claim 1, wherein the helical windings define a substantially helical axis without said helical windings surrounding a central core space.

12. The extraction device of claim 1, wherein the helical windings comprise less than five windings.

13. The extraction device of claim 1, wherein the helical windings define a linear length that comprises at least greater than one-tenth and less than one-half of a length of the embedding means.

14. The extraction device of claim 1, further comprising extraction means for extracting the embedding means and the portion of the tooth from a mouth of the patient.

15. The extraction device of claim 14, wherein the extraction means further comprises:

gripping means for gripping the embedding means when said embedding means is embedded in said portion of said tooth such that a proximal portion of said gripping means extends laterally outward from the embedding means;

handle means defining a central axis at a distal end thereof for receiving the proximal portion of the gripping means on said distal end; and locking means for locking the proximal portion of the gripping means to said handle means at any of a plurality of selectable positions of said proximal portion about the central axis of the handle means.

16. The extraction device of claim 1, wherein all portions of the distal body are formed to extend in a common, helical direction.

17. An extraction device for extracting at least a portion of a tooth from a patient, said extraction device comprising:

embedding means for becoming at least partially embedded within a portion of a tooth of a patient, said embedding means terminating in a distal body comprising a plurality of substantially helical windings extending in a generally proximal-to-distal direction, wherein at least a majority length of said distal body is characterized by an absence of a cylindrical, elongate linear core portion; and rotating means for rotating the embedding means to thereby embed at least a portion of the distal body of said embedding means into the portion of the tooth;

wherein the helical windings of the distal body comprise an external surface, and a proximal half and a distal half with respect to an axial direction, said helical windings further including a recess formed in the external surface thereof in the distal half of said helical windings of said distal body.

18. The extraction device of claim 17, wherein the recess is formed in a distal-most portion of the windings comprising less than one-half of one winding.

19. The extraction device of claim 18, wherein the recess is formed in a distal-most portion of the windings comprising less than one-third of one winding.

20. The extraction device of claim 18, wherein the recess is formed in a distal-most portion of the windings comprising less than one-fourth of one winding.

21. The extraction device of claim 18, wherein the recess is formed in a distal-most portion of the windings comprising less than one-fifth of one winding.

22. An extraction device for extracting at least a portion of a tooth from a patient, said extraction device comprising:

embedding means for becoming at least partially embedded within a portion of a tooth of a patient, said embedding means terminating in a distal body comprising a plurality of substantially helical windings extending in a generally proximal-to-distal direction, wherein at least a majority length of said distal body is characterized by an absence of a cylindrical, elongate linear core portion; and rotating means for rotating the embedding means to thereby embed at least a portion of the distal body of said embedding means into the portion of the tooth;

wherein the helical windings define a substantially helical axis, and wherein a cross-section of the helical windings taken orthogonal to the helical axis comprises a teardrop shape having a single point at one end thereof.

23. The extraction device of claim 22, wherein the shape of the cross-section comprises an exterior perimeter, said exterior perimeter having two opposing concave sections that are adjoined to form the single point.

24. The extraction device of claim 22, wherein the teardrop shape of the cross-section is substantially symmetrical.

25. An extraction device for extracting at least a portion of a tooth from a patient, said extraction device comprising:

embedding means for becoming at least partially embedded within a portion of a tooth of a patient, said embedding means terminating in a distal body comprising a plurality of substantially helical windings extending in a generally proximal-to-distal direction, wherein at least a majority length of said distal body is characterized by an absence of a cylindrical, elongate linear core portion; and rotating means for rotating the embedding means to thereby embed at least a portion of the distal body of said embedding means into the portion of the tooth;

wherein the rotating means comprises a manually operable gripping tool configured and adapted for gripping the embedding means when said embedding means is at least partially embedded within a portion of the tooth of the patient.

26. An extraction device for extracting at least a portion of a tooth from a patient, said extraction device comprising:

embedding means for becoming at least partially embedded within a portion of a tooth of a patient, said embedding means terminating in a distal body comprising a plurality of substantially helical windings extending in a generally proximal-to-distal direction, wherein at least a majority length of said distal body is characterized by an absence of a cylindrical, elongate linear core portion; and rotating means for rotating the embedding means to thereby embed at least a portion of the distal body of said embedding means into the portion of the tooth;

wherein the helical windings define a surrounding outer boundary that tapers radially inwardly in a proximal-to-distal direction.

27. An extraction device for extracting at least a portion of a tooth from a patient, said extraction device comprising:

embedding means for becoming at least partially embedded within a portion of a tooth of a patient, said embedding means terminating in a distal body comprising a plurality of substantially helical windings extending in a generally proximal-to-distal direction, wherein at least a majority length of said distal body is characterized by an absence of a cylindrical, elongate linear core portion;

rotating means for rotating the embedding means to thereby embed at least a portion of the distal body of said embedding means into the portion of the tooth; and gripping means for releasably gripping the embedding means when said embedding means is embedded in said portion of said tooth, said gripping means including a plurality of sliding members and a means for (i) sliding said sliding members radially inwardly into a locking position about the embedding means and (ii) sliding said sliding members radially outwardly into a releasing position.

28. An extraction device for extracting at least a portion of a tooth from a patient, said extraction device comprising:
a bit terminating in a distal body consisting of a plurality of substantially helical windings extending in a generally proximal-to-distal direction, such that said distal body is formed entirely of helical windings, said windings being sufficiently rigid to enable the distal body to become forcibly embedded in the portion of a tooth, and wherein the distal body is further characterized by an absence of a cylindrical, elongate linear core portion, and wherein said distal body is configured and adapted for being forcibly and at least partially embedded within the portion of a tooth of a patient.

29. The extraction device of claim 28, wherein the helical windings terminate in a tip portion having an open recess formed therein.

30. The extraction device of claim 28, wherein the distal body further comprises helical windings surrounding a central core space.

31. The extraction device of claim 28, wherein the helical windings define a substantially helical axis without said helical windings surrounding a central core space.

32. The extraction device of claim 28, all portions of the distal body are formed to extend in a common, helical direction.

33. An extraction device for extracting at least a portion of a tooth from a patient, said extraction device comprising:
a bit terminating in a distal body comprising a plurality of substantially helical windings extending in a generally proximal-to-distal direction, wherein at least a majority length of said helical windings is characterized by an absence of an elongate linear core portion separate from said helical windings, and wherein said distal body is configured and adapted for being forcibly and at least partially embedded within a portion of a tooth of a patient;
wherein the helical windings terminate in a tip portion having an open recess formed therein;
wherein the helical windings define a substantially helical axis, and wherein the recess comprises an elongate shape that extends in a generally nonparallel direction with respect to the helical axis.

34. An extraction device for extracting at least a portion of a tooth from a patient, said extraction device comprising:
a bit terminating in a distal body comprising a plurality of substantially helical windings extending in a generally proximal-to-distal direction, wherein at least a majority length of said helical windings is characterized by an absence of an elongate linear core portion separate from said helical windings, and wherein said distal body is configured and adapted for being forcibly and at least partially embedded within a portion of a tooth of a patient;
wherein the helical windings define a substantially helical axis, and wherein a cross-section of the helical windings taken orthogonal to the helical axis comprises a teardrop shape having a single point at one end thereof.

35. The extraction device of claim 34, wherein the shape of the cross-section comprises an exterior perimeter, said exterior perimeter having two opposing concave sections that are adjoined to form the single point.

36. An extraction device for extracting at least a portion of a tooth from a patient, said extraction device comprising:
embedding means for being embedded in a portion of a tooth of a patient;
gripping means for gripping the embedding means when said embedding means is embedded in said portion of said tooth such that a proximal portion of said gripping means extends laterally outward from the embedding means;
handle means defining a central axis at a distal end thereof for receiving the proximal portion of the gripping means on said distal end; and
locking means for locking the proximal portion of the gripping means to said handle means at any of a plurality of selectable positions of said proximal portion about the central axis of the handle means;
wherein the handle means comprises an elongate handle member defining an arch.

37. The extraction device of claim 36, wherein the locking means comprises a spring-loaded pin member.

38. The extraction device of claim 37, wherein the spring-loaded pin member is disposed in the distal end of the handle means.

39. The extraction device of claim 37, wherein the gripping means includes a receiving chamber formed therein, said receiving chamber being configured and adapted to receive the distal end of the handle means therein to, and wherein the spring-loaded pin member is disposed on the distal end of the handle means such that the spring maintains the pin forced laterally outwardly from said distal end absent some external force.

40. The extraction device of claim 39, wherein the gripping means includes sidewalls defining the receiving chamber, said sidewalls having a plurality of apertures formed therein for receiving the pin member therethrough when aligned with said pin member.

41. An extraction device for extracting at least a portion of a tooth from a patient, said extraction device comprising:
embedding means for being embedded in a portion of a tooth of a patient; and
gripping means for releasably gripping the embedding means when said embedding means is embedded in said portion of said tooth, said gripping means including a plurality of sliding members and a means for (i) sliding said sliding members radially inwardly into a locking position about the embedding means and (ii) sliding said sliding members radially outwardly into a releasing position.

42. The extraction device of claim 41, wherein the sliding members each include a beveled contacting face, and wherein the gripping means further comprises a manually operable button having beveled contacting faces disposed in slidable engagement against the beveled contacting faces of the sliding members.

43. The extraction device of claim 42, wherein the beveled contacting faces are configured and positioned to extend radially inward toward an axis of the button such that (i) depressing the button causes said button to slide along the beveled contacting faces of the sliding members to thereby force said sliding members radially outwardly, and (ii) releasing the button permits said sliding members to retract radially inwardly.

44. The extraction device of claim 41, wherein the gripping means comprises a casing, said extraction device further comprising lateral spring members disposed between the casing and the sliding members, respectively.

45. An extraction device for extracting at least a portion of a tooth from a patient, said extraction device comprising:

embedding means for becoming at least partially embedded within a portion of a tooth of a patient, said embedding means terminating in a distal body comprising a plurality of substantially helical windings extending in a generally proximal-to-distal direction, wherein at least a majority length of said distal body is characterized by an absence of a cylindrical, elongate linear core portion;

rotating means for rotating the embedding means to thereby embed at least a portion of the distal body of said embedding means into the portion of the tooth;

wherein the helical windings terminate in a tip portion having an open recess formed therein;

wherein the recess comprises a partial-spiral groove;

wherein the recess is formed in a distal-most portion of the windings comprising less than one-half of one winding;

wherein the helical windings define a substantially helical axis, and wherein the recess comprises an elongate shape that extends in a generally nonparallel direction with respect to the helical axis;

wherein a cross-section of the helical windings taken orthogonal to the helical axis comprises a teardrop shape having a single point at one end thereof, and wherein the shape of the cross-section comprises an exterior perimeter, said exterior perimeter having two opposing concave sections that are adjoined to form the single point;

wherein the embedding means further comprises a helical exterior edge formed on the distal body, and wherein the helical exterior edge is sharpened;

wherein the helical windings define a surrounding outer boundary that tapers radially inwardly in a proximal-to-distal direction;

wherein the helical windings comprise less than five windings, and wherein the helical windings define a linear length that comprises at least greater than one-tenth and less than one-half of a length of the embedding means;

extraction means for extracting the embedding means and the portion of the tooth from a mouth of the patient, wherein the extraction means further comprises:

gripping means for gripping the embedding means when said embedding means is embedded in said portion of said tooth such that a proximal portion of said gripping means extends laterally outward from the embedding means;

handle means defining a central axis at a distal end thereof for receiving the proximal portion of the gripping means on said distal end; and locking means for locking the proximal portion of the gripping means to said handle means at any of a plurality of selectable positions of said proximal portion about the central axis of the handle means.

46. The extraction device of claim 45, wherein the handle means comprises an elongate handle member defining an arch, and wherein the locking means comprises a spring-loaded pin member disposed in the distal end of the handle means, and wherein the gripping means includes a receiving chamber formed therein, said receiving chamber being configured and adapted to receive the distal end of the handle means therein to, and wherein the spring-loaded pin member is disposed on the distal end of the handle means such that the spring maintains the pin forced laterally outwardly from said distal end absent some external force.

47. The extraction device of claim 45, wherein the gripping means including a plurality of sliding members and a means for (i) sliding said sliding members radially inwardly into a locking position about the embedding means and (ii) sliding said sliding members radially outwardly into a releasing position;

wherein the sliding members each include a beveled contacting face, and wherein the gripping means further comprises a manually operable button having beveled contacting faces disposed in slidable engagement against the beveled contacting faces of the sliding members;

wherein the beveled contacting faces are configured and positioned to extend radially inward toward an axis of the button such that (i) depressing the button causes said button to slide along the beveled contacting faces of the sliding members to thereby force said sliding members radially outwardly, and (ii) releasing the button permits said sliding members to retract radially inwardly;

wherein the gripping means includes sidewalls defining the receiving chamber, said sidewalls having a plurality of apertures formed therein for receiving the pin member therethrough when aligned with said pin member.

48. A method of extracting at least a portion of a tooth from a mouth of a patient, said method comprising the steps of:

(a) inserting a bit into a motorized boring instrument;

(b) activating the motorized boring instrument and boring the bit into the portion of the tooth and lodging at least a portion of the bit into a position of stability in the portion of the tooth;

(c) attaching an arched handle to the bit; and (d) extracting the portion of the tooth by elevating the arched handle without maintaining any force-distributing member in a static position against any teeth of the patient.

* * * * *